United States Patent [19]

Tessitore

[11] Patent Number: 4,478,846
[45] Date of Patent: Oct. 23, 1984

[54] 2-(1-ALKYL-5-NITRO)-IMIDAZOLYL-1-(2-HYDROXY-5-ALKYL)-PHENYL CARBINOLS AND PHARMACEUTICAL COMPOSITIONS CONTAINING THEM

[76] Inventor: Pietro T. Tessitore, Via Dante Alighieri, 71, 18038 Sanremo, Italy

[21] Appl. No.: 545,251

[22] Filed: Oct. 25, 1983

[30] Foreign Application Priority Data

Oct. 27, 1982 [IT] Italy .............................. 23944 A/82

[51] Int. Cl.$^3$ .................. C07D 233/91; A61K 31/415
[52] U.S. Cl. .................................. 424/273 R; 548/339
[58] Field of Search .................... 548/339; 424/273 R

[56] References Cited

FOREIGN PATENT DOCUMENTS 2436780  4/1980  France.
2504134 10/1982  France.

Primary Examiner—Robert W. Ramsuer
Attorney, Agent, or Firm—Stevens, Davis, Miller & Mosher

[57] ABSTRACT 2-(1-Alkyl-5-nitro)-imidazolyl-1-(2-hydroxy-5-alkyl)-phenyl carbinols endowed with antiprotozoal activity, action against mycetes and anaerobic germs, but without mutagenic action; method for the preparation thereof and pharmaceutical compositions containing them.

4 Claims, No Drawings

2-(1-ALKYL-5-NITRO)-IMIDAZOLYL-1-(2-HYDROXY-5-ALKYL)-PHENYL CARBINOLS AND PHARMACEUTICAL COMPOSITIONS CONTAINING THEM

This invention relates to new 5-nitroimidazole derivatives, endowed with antiprotozoal action, action against mycetes and anaerobic germs, to the method for preparing them and to the pharmaceutical compositions containing them.

More particularly, this invention relates to new 2-(1-alkyl-5-nitro)-imidazolyl-1-(2-hydroxy-5-alkyl)-phenyl carbinols.

Several antiprotozoal compounds are known, expecially interesting because of their effectiveness against Trychomonas Vaginalis, which causes one of the more frequent and always increasing venereal infections.

As known, 1-(2-hydroxyethyl)-2methyl-5-nitroimidazole (U.S. Pat. No. 2,944,061), 1-methyl-2[(carbamoyloxy)-methyl]-5-nitroimidazole (U.S. Pat. No. 3,450,710; U.S. Pat. No. 3,450,764), 1-[2-(ethylsulfonyl)-ethyl]-2-methyl-5-nitroimidazole (U.S. Pat. No. 3,376,311) and 2-amino-4-[2-(1-methyl-5-nitro-2-imidazolyl)-vinyl]-pyrimidine (U.S. Pat. No. 3,969,520), have obtained a great success in chemotherapy because of their remarkable activity and favourable therapeutic index. All the above mentioned drugs are 5-nitroimidazoles bearing different substituents on positions 1 and 2 of the imidazole nucleus. They are very efficacious, particularly against Trychomonas Vaginalis, but their use is limited by some disadvantages. For instance, they are inactive against mycetes and in particular against Candida Albicans which more and more frequently occurs in the infections caused by Trychomonas Vaginalis. A further disadvantage is their mutagenic action. The former disadvantage is overcome in the medical parctice by administering a drug efficacious against Trychomonas Vaginalis and a drug efficacious against mycetes. However, this practice is inconvenient to patients.

The latter disadvantage, the mutagenic action of the above mentioned drug is a serious problem for the sanitary authorities in all Countries in the world because of the involved risks.

Positive results have been recently attained by associating Metronidazole with an antioxidizing compound, e.g. 2(3)-tert.butyl-4-hydroxyanisole.

However, also in this case, the inconvenience due to the different pharmacocinetic properties of the associated drugs are not avoided. The present invention relates to new 5-nitroimidazole derivatives containing in their molecule groups suitable for hindering the mutagenic action, according to Bruckner, Bueding and Voge (j. Prasitol. 65(3),473–474 (1970).

Surprisingly, the compounds of this invention are efficacious not only against Trichomonas Vaginalis, but also against Candida Albicans and against some anaerobic germs.

More particularly, the compounds of this invention have the following general formula:

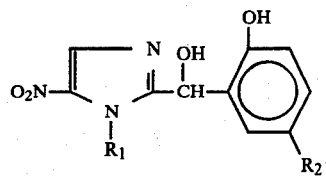

wherein:
R$_1$ represents a straight or branched alkyl radical containing from 1 to 4 carbon atoms or is hydroxyalkyl or chloroalkyl;
R$_2$ represents a straight or branched alkyl radical containing from 1 to 6 carbon atoms.

Exemplary of the compounds of this invention is 2-(1-methyl-5-nitro)-imidazolyl-1-(2-hydroxy-5-tert.butyl)-phenyl-carbinol because of its pharmacological and therapeutical properties.

The compounds of this invention are prepared by the method described in the literature for the synthesis of triphenylmethanes (G. Casiraghi et al. J. C. S. Perkin I, 2077 (1974)), wherein an aromatic aldehyde is reacted with aryloxymagnesium bromide, in the molar ratio 1:2.

The Applicant has now found that 5-nitroimidazole derivatives of this invention may be prepared by the above mentioned reaction wherein the aromatic aldehyde is replaced by a heterocyclic aldehyde, in particular 1-methyl-5-nitro-2-carboxyaldehyde.

More particularly, the Applicant has found that by reacting 1 mol of the heterocyclic aldehyde with 1 mol of aryloxymagnesium halide there are obtained the 5-nitroimidazole derivatives of this invention, that is carbinols containing a heterocyclic ring, in particular the 5-nitro-imidazole ring, and an aromatic ring, in particular a phenol bearing a straight or branched alkyl radical having from 1 to 6 carbon atoms in the position 4 in respect to the —OH group.

Therefore, it is a further object of the present invention the method for the preparation of 5-nitro-imidazole derivatives of this invention.

The reaction conditions are those described by Casiraghi et al. (J. C. S. Perkin I, 2077 (1974).

2-(1-methyl-5-nitro)-imidazolyl-1-(2-hydroxy-5-tert.butyl)-phenyl-carbinol, that is the exemplary compound, when tested according to Aimes shows a mutagenic action which is about 1/10 of the mutagenic action of the nitroimidazoles on the market (Flagyl ,Azanidazole).

2-(1-methyl-5-nitro)-imidazolyl-1-(2-hydroxy-5-tert.butyl)-phenyl carbinol is effective for the treatment of vaginites caused by protozoal agents and mycetes, both for topic and systemic application.

Activity in vitro of the compound is variable according to the various Trychomonas Vaginalis strains and is generally between 0.2 and 0.5 mg/ml.

When administered by oral route or by injection route, this compound gives particularly high concentration in the vaginal secretum. By administering 500 mg to voluntary healthy patients, the peak in the vaginal secretum is reached 3 hours after the administration of the drug.

The excretion occurs for about 13% by urinary way and 70% by fecal route. The administered compound represents the main part of the excreted product and two metabolites are present which have been proven to be oxidation products of the aromatic ring of the molecule. Furthermore, traces of the compound, deriving from the reduction of the nitro group of the imidazole ring have been found.

The product did not cause any lesion to the mucose of the gastrointestinal apparatus when applied by oral route. No lesion is caused by topical application of the product in the healthy or inflamed vagina.

2-(1-methyl-5-nitro)imidazolyl-1-(2-hydroxy-5-tert.-butyl)-phenyl carbinol is also effective for the treatment of infections caused by anaerobic germs.

The action against mycetes and anaerobic germs has been proven by the generally used microbiological methods.

The pharmacological characteristics of 2-(1-methyl-5-nitro)-imidazolyl-1-(2-hydroxy-5-tert.butyl)-phenyl carbinol correspond to those of Azanidazole; relevant undesired effects are absent. $LD_{50}$ for the tested species is 10% higher than $LD_{50}$ of Azanidazole, either by i.p. route or per os.

The compounds of this invention may be formulated as vaginal inserts, for the topic use, or as capsules or tablets for the administration per os.

For the treatment either of the infections caused by Trychomonas Vaginalis or of the infections caused by anaerobic germs the drug may be administered by i.v. route.

The following example is given to illustrate this invention without limiting it in any way.

EXAMPLE

Preparation of 2-(1-methyl-5-nitro)-imidazolyl-1-(2-hydroxy-5-tert.butyl-phenyl carbinol 150 g (1 mol) of p-tert.butylphenol are dissolved in 1200 ml of anhydrous ethyl ether and the thus obtained solution is added to a 10% solution of ethylmagnesium bromide in 1000 ml of anhydrous ether, at room temperature, under stirring.

After having evaporated the ether, 1000 ml of anhydrous benzene are added and the mixture is distilled, at normal pressure, until its volume is about ⅔ of the original volume. After cooling at room temperature, 1 mol of 1-methyl-5-nitro-imidazolyl-2-carboxyaldehyde in 1000 ml of anhydrous benzene is added.

The whole is boiled for 1 hour, is cooled to about 10° C. and is added with 8% HCl to adjust the pH to 7.

Benzene layer is dried and concentrated up to ⅔ of the volume. The desired product is allowed to crystallize. m.p. 158°–160° C.; yield 50–60%.

IR and NMR spectra are in agreement with the foreseen structure. Both the heterocyclic aldehyde and phenol necessary for the synthesis are available on the market.

I claim:

1. 2-(1-alkyl-5-nitro)-imidazolyl-1-(2-hydroxy-5-alkyl)-phenyl carbinols of the general formula:

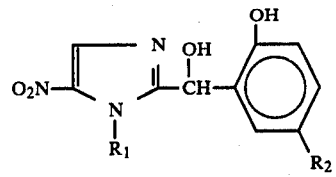

wherein $R_1$ represents a straight or branched alkyl radical having from 1 to 4 carbon atoms, or is hydroxyalkyl or chloroalkyl;

$R_2$ is a straight or branched alkyl radical having from 1 to 6 carbon atoms.

2. 2(1-methyl-5-nitro)-imidazolyl-1-(2-hydroxy-5-tert.butyl)-phenyl carbinol.

3. Pharmaceutical compositions for the treatment of protozoal infections, of infections caused by anaerobic germs and of infections caused by mycetes, characterized in that they contain a compound of the general formula:

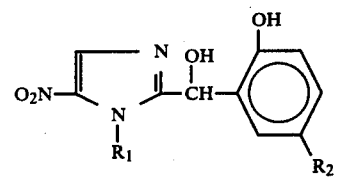

(wherein $R_1$ represents a straight or branched alkyl radical, having from 1 to 4 carbon atoms, or is hydroxyalkyl or chloroalkyl; $R_2$ represents a straight or branched alkyl radical having from 1 to 6 carbon atoms) as active ingredient together with pharmaceutically acceptable carriers.

4. Pharmaceutical compositions for the treatment of protozoal infections, or infections caused by anaerobic germs and infections caused by mycetes, characterized in that they contain 2-(1-methyl-5-nitro)-imidazolyl-1-(2-hydroxy-5-tert.butyl)-phenyl carbinol as active ingredient together with pharmaceutically acceptable carriers.

* * * * *